United States Patent [19]

Morwick et al.

[11] 4,420,479
[45] Dec. 13, 1983

[54] OLEFINIC BENZIMIDAZOLES, FORMULATIONS, AND ANTIVIRAL METHODS

[75] Inventors: Tina M. Morwick; Charles J. Paget, both of Indianapolis; James H. Wikel, Greenwood, all of Ind.

[73] Assignee: Eli Lilly and Company, Indianapolis, Ind.

[21] Appl. No.: 366,760

[22] Filed: Apr. 8, 1982

[51] Int. Cl.³ .................. A61K 31/415; C07D 235/30
[52] U.S. Cl. ................................. 424/246; 424/248.5; 424/260; 424/270; 424/273 B; 542/426; 544/54; 544/56; 544/139; 546/199; 548/181; 548/306

[58] Field of Search ............... 548/306, 181; 546/199; 544/54, 55, 139; 542/426; 424/246, 248.5, 267, 270, 273 B

[56] References Cited

U.S. PATENT DOCUMENTS

| | | | |
|---|---|---|---|
| 4,150,028 | 4/1979 | Paget et al. | 260/306.7 |
| 4,174,454 | 11/1979 | Paget et al. | 548/306 |
| 4,230,868 | 10/1980 | Paget et al. | 548/306 |

*Primary Examiner*—Richard Raymond
*Attorney, Agent, or Firm*—Charles W. Ashbrook; Arthur R. Whale

[57] ABSTRACT

1-Substituted-2-amino-5(or 6) olefinic benzimidazoles and intermediates therefor are disclosed. The compounds are potent antiviral agents. Pharmaceutical formulations containing such compounds and a method of treating viral infections are provided.

46 Claims, No Drawings

OLEFINIC BENZIMIDAZOLES, FORMULATIONS, AND ANTIVIRAL METHODS

BACKGROUND OF THE INVENTION

This invention relates to a new class of benzimidazole compounds characterized by the presence of a substituted olefinic moiety in the aryl ring. The new compounds have a broad spectrum of antiviral activity.

A wide variety of benzimidazoles are known in the art. Numerous 2-benzimidazole carbamates have found widespread use in the veterinary field as anthelmintic agents for ruminants; see U.S. Pat. No. 4,159,337. Several 2-amino-benzimidazoles have been disclosed to have anti-inflammatory activity; see U.S. Pat. No. 3,825,537. Considerable interest recently has focused on benzimidazoles as antiviral agents; see U.S. Pat. Nos. 4,150,028, 4,018,790 and 4,008,243. Various aryl substituted alkylidenemethyl benzimidazoles have been disclosed by Paget et al. in U.S. Pat. No. 4,118,742. The compounds of the latter reference differ from those now claimed since the reference compounds require an alkylidene grouping whereas the present compounds will not permit such grouping.

SUMMARY OF THE INVENTION

This invention concerns a group of compounds characterized as 5 or 6-substituted ethylenic benzimidazoles. The invention additionally is directed to a method of using such compounds, as well as formulations containing the same and intermediates therefor. The invention is more particularly directed to benzimidazoles defined by the general formula

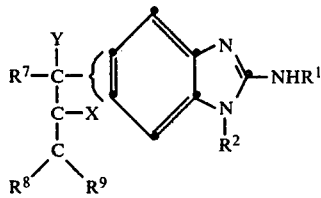

wherein:
$R^1$ is hydrogen or $C_1$-$C_4$ alkanoyl;
$R^2$ is hydrogen, —$SO_2R^3$ or a group of the formula

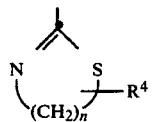

in which:
$R^3$ is $C_1$-$C_5$ alkyl, $C_3$-$C_7$ cycloalkyl, phenyl, furyl, thienyl, or $R^5R^6N$, wherein $R^5$ and $R^6$ independently are $C_1$-$C_3$ alkyl, or taken together with the nitrogen to which they are attached are pyrrolidino, piperidino or morpholino;
$R^4$ is hydrogen, $C_1$-$C_3$ alkyl, phenyl, or benzyl; and n is 2 or 3;
$R^7$ is hydrogen, $C_1$-$C_7$ alkyl, $C_3$-$C_7$ cycloalkyl, ($C_3$-$C_7$ cycloalkyl)methyl, 1-($C_3$-$C_7$ cycloalkyl)ethyl, phenyl, or substituted phenyl;
X is hydrogen and Y is hydroxy, or together X and Y form a bond;
$R^8$ and $R^9$ independently are hydrogen, halo, cyano, nitro,

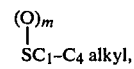

$CH_2R^{10}$, $COR^{10}$, phenyl, or substituted phenyl;
m is 0, 1 or 2;
$R^{10}$ is hydroxy, $C_1$-$C_4$ alkoxy, $C_1$-$C_4$ alkanoyloxy, halo, $C_3$-$C_6$ cycloalkyl-$C_1$-$C_4$ alkoxy, or (O—C-1-$C_4$ alkyl)$_y$ $NR^{11}R^{12}$; where
y is 0 or 1; and
$R^{11}$ and $R^{12}$ independently are hydrogen or $C_1$-$C_4$ alkyl;
provided that one and only one of $R^8$ and $R^9$ is hydrogen, except when either of $R^8$ or $R^9$ is halo, the other may be halo, and when Y is hydroxy, $R^8$ and $R^9$ are other than halo; and the pharmaceutically acceptable acid addition salts thereof.

Compounds of the above formula wherein X and Y together are a bond are referred to herein as "olefinic benzimidazoles". The compounds wherein X is hydrogen and Y is hydroxy are antiviral agents as well as intermediates for the olefinic benzimidazoles, and are referred to as "benzimidazole carbinols".

Preferred olefinic benzimidazoles comprehended by this invention have the above formula wherein $R^1$ is hydrogen. Additionally preferred compounds within such group are those defined by the above formula wherein $R^2$ is $SO_2R^3$, $R^3$ is $C_1$-$C_5$ alkyl or $R^5R^6N$, wherein $R^5$ and $R^6$ independently are $C_1$-$C_3$ alkyl.

Additionally preferred compounds have the above formula wherein $R^2$ is 2-thiazolinyl or 2-thiazinyl.

Further preferred compounds are defined by the above formula wherein $R^7$ is phenyl and $R^8$ and $R^9$ independently are halo, cyano, or $COR^{10}$ wherein $R^{10}$ is $C_1$-$C_4$ alkoxy or $NR^{11}R^{12}$.

This invention additionally provides a method of treatment which comprises administering to a subject suffering from a viral infection or suspected of developing a viral infection an antiviral amount of a benzimidazole defined by the above formula. A preferred method of treatment comprises administering an antiviral amount of an olefinic benzimidazole as above defined.

A further embodiment of the present invention includes a pharmaceutical formulation useful in the treatment and prophylactic control of viral infections in mammals comprising a benzimidazole defined by the above general formula in combination with a pharmaceutically acceptable carrier or diluent therefor. Preferred formulations are those having an olefinic benzimidazole as active ingredient.

DETAILED DESCRIPTION OF THE INVENTION

The present invention provides a group of benzimidazole antiviral agents that are substituted at the 5 or 6 position with a carbinol or an olefinic moiety. The benzimidazoles are potent antiviral agents and are accordingly useful in the treatment and control of viral growth, including growth attributable to rhinovirus, polio, coxsackie, echo virus, mengo virus, influenza, and related viral growths.

As pointed out in the above general formula defining the compounds of this invention, the amino group attached to the benzimidazole 2-position may be substituted or unsubstituted, i.e. $R^1$ is hydrogen or $C_1$-$C_4$ alkanoyl. The preferred compounds are those wherein $R^1$ is hydrogen. The term "$C_1$-$C_4$ alkanoyl" includes formyl, acetyl, propionyl, butyryl and isobutyryl. Compounds wherein $R^1$ is alkanoyl are prepared by simply acylating a 2-aminobenzimidazole with any of a number of common acylating agents, for instance acetyl chloride, butyryl anhydride, and the like.

The olefinic benzimidazoles of the invention, and the benzimidazole carbinols, are substituted at the one position of the benzimidazole nucleus by a sulfonyl group or by a thiazolinyl or thiazinyl moiety. These substituents are defined in the above formula by $R^2$. When $R^2$ is thiazolinyl or thiazinyl, the groups may bear a substituent selected from alkyl, phenyl or benzyl. Examples of such groups include 4-methylthiazolinyl, 5-phenylthiazinyl, and 5-benzylthiazinyl. Preferred compounds of the invention are the sulfonyl benzimidazoles wherein $R^2$ is —$SO_2R^3$, particularly when $R^3$ is $C_1$-$C_5$ alkyl or dialkylamino. The term "$C_1$-$C_5$ alkyl" embraces groups such as methyl, ethyl, isopropyl, n-propyl, isobutyl, and isopentyl. Dialkylamino refers to groups of the formula $R^5R^6N$, wherein $R^5$ and $R^6$ independently are $C_1$-$C_3$ alkyl, and such groups include dimethylamino, methylethylamino, diisopropylamino, ethyl-n-propylamino, and the like. $R^3$ may additionally be a $C_3$-$C_7$ cycloalkyl group such as cyclopropyl, cyclobutyl, cyclohexyl and cycloheptyl. Similarly, $R^5$ and $R^6$ may complete a cyclic nitrogen containing ring selected from pyrrolidino, piperidino and morpholino.

In the above formula, $R^7$ includes $C_1$-$C_7$ alkyl groups such as methyl, ethyl, isopropyl, tert-butyl, n-hexyl, 3-methylhexyl and the like. Examples of $R^7$ when it defines a $C_3$-$C_7$ cycloalkyl group include cyclopropyl, cyclobutyl, cyclopentyl and cycloheptyl. The term $R^7$ additionally can mean phenyl or substituted phenyl, and by the latter term is meant a phenyl group substituted with one group selected from hydroxy, halo, $C_1$-$C_4$ alkyl, $C_1$-$C_4$ alkoxy, nitro or trifluoromethyl. A preferred $R^7$ moiety is phenyl. Another preferred $R^7$ moiety is 4-methoxyphenyl. Other substituted phenyl groups defined by $R^7$ include 3-hydroxyphenyl, 4-tert.-butylphenyl, 2-methylphenyl, 3-nitrophenyl, 3-trifluoromethylphenyl, 4-chlorophenyl, 3-bromophenyl and the like.

The following definitions are presented to illustrate the scope of $R^8$ and $R^9$ in the above formula. As used herein, "halo" includes fluoro, bromo, chloro and iodo, and preferred halo groups are bromo and chloro. The term

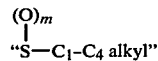

refers to thio, sulfinyl and sulfonyl groups having attached thereto a straight or branched carbon chain of one to four carbon atoms. Examples of such groups include methylthio, ethylthio, isobutylthio, ethylsulfinyl, isobutylsulfinyl, isopropylsulfonyl, n-butylsulfonyl, tert-butylsulfonyl and the like.

The term "$COR^{10}$" refers to a carboxylic acid group when $R^{10}$ is hydroxy, to alkyl esters when $R^{10}$ is $C_1$-$C_4$ alkoxy (e.g. methoxycarbonyl, tert-butoxycarbonyl), and to cycloalkyl $C_1$-$C_4$ alkyl esters when $R^{10}$ is $C_3$-$C_6$ cycloalkyl-$C_1$-$C_4$ alkoxy (eg. 2-cyclopentylethoxy), cyclohexylmethoxy. The term "$COR^{10}$" additionally includes amides when $R^{10}$ is (O—$C_1$-$C_4$ alkyl)$_y$ $NR^{11}R^{12}$ and y is zero. Such amides are thus defined by the term "$CONR^{11}R^{12}$" where $R^{11}$ and $R^{12}$ independently are hydrogen or $C_1$-$C_4$ alkyl. When y is one and $R^{10}$ is (O—$C_1$-$C_4$ alkyl)$_y NR^{11}R_{12}$, the group defined is an aminoalkyl ester of the formula $COOC_1$-$C_4$ alkyl $NR^{11}R^{12}$, wherein $R^{11}$ and $R^{12}$ independently are hydrogen or $C_1$-$C_4$ alkyl. Such groups include dimethylaminomethoxycarbonyl, 3-(N-ethyl-N-methylamino)propoxycarbonyl, and the like.

The terms $R^8$ and $R^9$ additionally define phenyl or substituted phenyl, wherein the latter term is a monosubstituted phenyl group in which the substituent is selected from hydroxy, halo, $C_1$-$C_4$ alkyl, $C_1$-$C_4$ alkoxy, nitro or trifluoromethyl. As noted above, a preferred substituted phenyl group is 4-methoxyphenyl.

Compounds of the invention wherein one of $R^8$ or $R^9$ is $COR^{10}$ can be reduced to give compounds wherein $R^8$ or $R^9$ is $CH_2R^{10}$, and $R^{10}$ is as defined above. When $R^{10}$ is hydroxy, $R^8$ or $R^9$ define a hydroxymethyl group. When $R^{10}$ is $C_1$-$C_4$ alkoxy, the term $CH_2R^{10}$ is an alkoxymethyl group such as methoxymethyl or isobutoxymethyl. When $R^{10}$ is $C_1$-$C_4$ alkanoyloxy, the term $CH_2R^{10}$ is an alkanoyloxymethyl group such as acetoxymethyl, propionoxymethyl butyroxymethyl and the like. When $R^{10}$ is halo, the term $CH_2R^{10}$ is a halomethyl group such as chloromethyl or bromomethyl. When $R^{10}$ is $C_3$-$C_6$ cycloalkyl-$C_1$-$C_4$ alkoxy, the term $CH_2R^{10}$ includes cyclopropylmethoxymethyl, 3-cyclohexylpropoxymethyl and the like. When $R^{10}$ is (O—$C_1$-$C_4$ alkyl)$_y NR^{11}R^{12}$, the term $CH_2R^{10}$ includes dimethylaminomethyl, dimethylaminomethoxymethyl, and 4-diethylaminobutoxymethyl.

The olefinic benzimidazole compounds provided by this invention can be prepared employing any number of chemical processes well known to those skilled in the art of organic chemistry. For example, the antiviral olefinic benzimidazoles of this invention having the above formula wherein one or both of $R^8$ and $R^9$ are halo can be prepared by direct halogenation of a 5 or 6-(α-methylenemethyl)benzimidazole derivative. Such reaction can be depicted by the following general scheme:

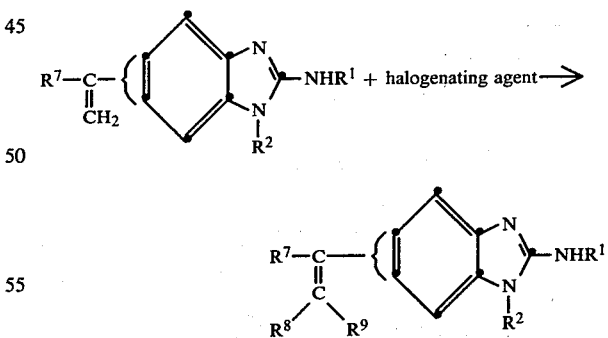

wherein $R^1$, $R^2$ and $R^7$ are as defined above, and $R^8$ and $R^9$ independently are hydrogen or halo, except that at least one of $R^8$ and $R^9$ is halo.

The methylenemethyl benzimidazoles which are required as starting materials for the halogenation reaction are readily available by the method described in U.S. Pat. No. 4,118,742. The halogenating agents commonly utilized in the halogenation reaction include N-chlorosuccinimide and N-bromosuccinimide. The halogenation reaction generally is carried out by combining the benzimidazole with the halogenating agent in a suitable unreactive organic solvent such as benzene, tetrahydrofuran, chloroform, toluene, diethyl ether, or related solvents. The use of about an equimolar quantity of halogenating agent effects monohalogenation to give a compound wherein one of $R^8$ and $R^9$ is halo and the other is hydrogen. The use of a two molar amount or larger excess of halogenating agent effects dihalogenation and produces a compound wherein $R^8$ and $R^9$ both are halo. The reaction generally is carried out at a temperature of about 20° to about 80° C., and normally is complete within about one to about seventy-two hours at such temperature. The product is isolated by simply cooling the reaction mixture and removing the reaction solvent, for instance by evaporation under reduced pressure. The compounds thus prepared can be further purified if desired by chromatography, crystallization or the like.

It will be recognized that a mono-halogenated compound, i.e. wherein one of $R^8$ and $R^9$ is halo and the other is hydrogen, can be further halogenated if desired, with the same or a different halogenating agent. For instance, reaction for about one hour of a methylene benzimidazole starting material such as 1-phenylsulfonyl-2-acetamido-5-(α-methylenecyclobutylmethyl)benzimidazole with about one equivalent of a halogenating agent such as N-chlorosuccinimide effects monohalogenation to provide 1-phenylsulfonyl-2-acetamido-5-(α-chloromethylenecyclobutylmethyl)-benzimidazole. Reaction of the latter compound with about one equivalent or an excess of an agent such as N-bromosuccinimide effects further halogenation to give 1-phenylsulfonyl-2-acetamido-5-(α-bromo-α-chloromethylenecyclobutylmethyl)benzimidazole.

The olefinic benzimidazoles of this invention defined by the above general formula wherein $R^8$ and $R^9$ are other than halo are prepared by dehydration of a 5 or 6-α-hydroxymethylbenzimidazole derivative. Such dehydration reaction of a benzimidazole carbinol is depicted by the following generalized scheme:

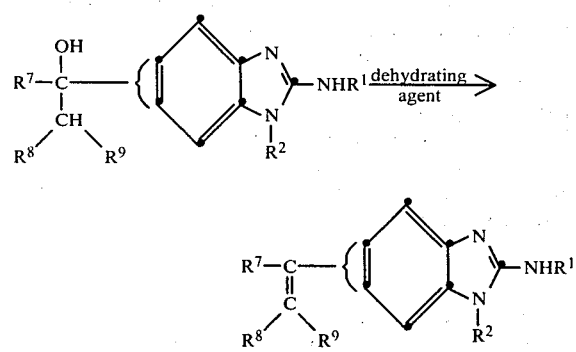

wherein $R^1$, $R^2$ and $R^7$ have the above-defined meanings while $R^8$ and $R^9$ are as defined above, other than halo.

The dehydration of a benzimidazole carbinol according to the above scheme is accomplished by reaction of the carbinol with any of a number of dehydrating agents which are capable of removing a mole of water from each mole of carbinol to thus provide the corresponding olefinic benzimidazole of the invention. Typical dehydrating agents commonly used include acids such as sulfuric acid, hydrochloric acid, formic acid, polyphosphoric acid and p-toluenesulfonic acid. In a routine dehydration reaction, a carbinol is combined with about an equal weight amount or an excess of a dehydrating agent. The reaction normally is carried out in an organic solvent such as chloroform, benzene, dichloromethane, or the like, and ideally is conducted at a temperature of about 20° to about 80° C., for instance at room temperature or at the reflux temperature of the particular solvent utilized for the reaction. Under these conditions, the dehydration typically is substantially complete within about one to about forty-eight hours. Longer reaction periods may be employed if desired. Upon completion of the dehydration reaction, the product, an olefinic benzimidazole of the invention, can be isolated by simply washing the reaction mixture with a base, for instance dilute aqueous sodium bicarbonate or the like, and removing the organic reaction solvent by evaporation. The product can be further purified if desired by normal methods, including chromatography and crystallization from solvents such as ethanol, ethyl acetate, acetone, and the like.

It should be noted that when $R^8$ and $R^9$ in the above general formula defining the olefinic benzimidazoles of this invention are different, the compounds exist as cis (or Z) and trans (or E) isomers. The dehydration reaction described above generally provides a mixture of such isomers. For example, dehydration of a compound such as 1-methylsulfonyl-2-amino-5-(α-hydroxy-α-ethylsulfinylmethylcyclopropylethyl)benzimidazole affords a mixture of cis-1-methylsulfonyl-2-amino-5-(α-ethylsulfinylmethylenecyclopropylethyl)benzimidazole, and the corresponding trans isomer. The cis and trans isomers of the benzimidazoles provided herein are represented by the general formulas:

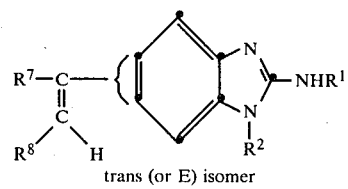
trans (or E) isomer

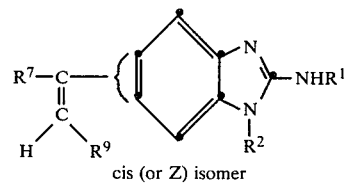
cis (or Z) isomer

Since both the cis and the trans olefinic benzimidazoles of this invention are potent antiviral agents, they can be utilized in the treatment of viral infections either alone or as a mixture.

Isolation of pure cis and pure trans olefinic benzimidazoles of the invention generally is accomplished by chromatography or by crystallization or fractional crystallization from solvents such as methanol, ethanol, acetone, or the like. The trans isomers appear more active than the cis compounds, and therefore are preferred over the cis isomers.

The benzimidazole carbinols which are the required starting materials in the above-described dehydration reaction are themselves antiviral agents and are provided in a further embodiment of this invention. Such carbinols are prepared by reaction of a 5 or 6 carbonyl substituted benzimidazole with a suitably substituted carbanion. For example, a carbanion of the formula $R^8 CH_2^\ominus$ or $R^9 CH_2^\ominus$, wherein $R^8$ and $R^9$ are as defined above other than halo, reacts with a carbonyl benzimidazole of the formula

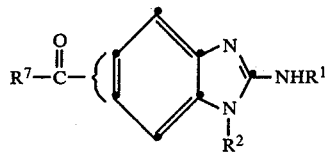

to form the corresponding benzimidazole carbinol. The carbonyl benzimidazoles are available by the method of U.S. Pat. No. 4,118,742. The requisite carbanions are formed by reaction of an active methylene compound with a strong base such as methyl lithium, n-butyl lithium, lithium diisopropylamide, potassium tert.-butoxide, and the like. Active methylene compounds are those which have an electronegative functional group attached to a methyl or methylene group. Typical active methylene compounds which readily form carbanions include compounds of the formulas $CH_3CN$, $CH_3NO_2$, $CH_3SOC_1-C_4$ alkyl, $CH_3SO_2C_1-C_4$ alkyl, $CH_3SC_1-C_4$ alkyl, and $CH_3COR^{10}$, wherein $R^{10}$ has the above-defined meaning. Such compounds generally are reacted with about an equimolar quantity or an excess of strong base in an unreactive organic solvent such as diethyl ether, tetrahydrofuran, dioxane, diglyme, and the like. For example, an active methylene compound such as phenylacetate can be reacted with a strong base such as n-butyl lithium in a solvent such as diethyl ether to form the corresponding carbanion, namely lithium phenoxycarbonylcarbanion. Such reactions typically are carried out at a temperature of about $-78°$ to about $-50°$ C., and are substantially complete within about one to about six hours. Active methylene compounds which possess a functional group with acidic hydrogen atoms are preferably protected prior to reaction with a strong base. Typical protecting groups include silyl derivatives such as silyl ethers and silyl esters.

Once the carbanion has formed, it typically is not isolated, but rather is reacted in situ with a carbonyl benzimidazole derivative. For example, nitro methane can be reacted with a base such as sodium hydroxide in a solvent such as tetrahydrofuran to form the corresponding carbanion, which can then be reacted in situ with a benzimidazole such as 1-methylsulfonyl-2-amino-5-acetylbenzimidazole by simply adding the carbonyl benzimidazole to the reaction mixture. The carbanion generally is utilized in an excess of about 1 to about 10 molar compared to the carbonyl benzimidazole, and the reaction is routinely carried out at a temperature of about $-70°$ to about 30° C. The product of the reaction is the aforementioned carbinol benzimidazole, and can be isolated by simply acidifying the reaction mixture, for example with hydrochloric acid, and then removing the reaction solvent, for instance by evaporation under reduced pressure. Further purification of the carbinol benzimidazole generally is not needed, but if desired can be accomplished by routine procedures such as chromatography, crystallization, and the like.

The olefinic benzimidazoles that are prepared by halogenation or by dehydration of a benzimidazole carbinol as heretofore described are useful as antiviral agents, and additionally are important intermediates leading to other olefinic benzimidazoles of the invention. For instance, olefinic benzimidazoles defined by the above general formula wherein one of $R^8$ and $R^9$ are $COR^{10}$ and $R^{10}$ is alkoxy such as tert.-butoxy can be reacted with an acid such as paratoluenesulfonic acid to effect saponification to the corresponding carboxylic acid derivative, namely an olefinic benzimidazole wherein one of $R^8$ and $R^9$ is $COR^{10}$ and $R^{10}$ is hydroxy. The carboxylic acid so formed can be re-esterified if desired with the same or a different ester forming goup, or alternatively can be converted to an anhydride (wherein $R^{10}$ is $C_1-C_4$ alkanoyloxy) or to an amine derivative or amide or substituted amide (where $R^{10}$ is $(O-C_1-C_4 \text{ alkyl})_y NR^{11}R^{12}$) by conventional procedures. Moreover, olefinic benzimidazoles of the invention wherein $R^8$ or $R^9$ is $COR^{10}$, for instance a compound such as 1-phenylsulfonyl-2-amino-5(or 6)-($\alpha$-N,N-diethylaminocarbonylmethylenebenzyl)benzimidazole, can be reduced by reaction with a reducing agent such as diborane or the like to provide the corresponding olefinic benzimidazole of the above general formula wherein one of $R^8$ and $R^9$ is $CH_2R^{10}$, for instance 1-phenylsulfonyl-2-amino-5(or 6)-($\alpha$-N,N-diethylaminoethylenebenzyl)benzimidazole. When $R^8$ or $R^9$ is $CH_2R^{10}$ and $R^{10}$ is hydroxy, normal acylation provides compounds wherein $R^8$ or $R^9$ is $CH_2-C_1-C_4$ alkanoyloxy.

The 2-aminobenzimidazoles of this invention, i.e. compounds of the above formula wherein $R^1$ is hydrogen, can be acylated by reaction with a $C_1-C_4$ alkanoyl acylating agent, preferably an acid halide or anhydride such as acetyl chloride, formic acetic anhydride, or the like.

The compounds of this invention wherein $R^2$ is $-SO_2R^3$ are useful as antiviral agents and as intermediates. Such compounds, when reacted with an aqueous base such as sodium hydroxide, are converted to benzimidazoles unsubtituted at the 1-position, i.e. compounds wherein $R^2$ is hydrogen. These latter compounds are readily re-acylated with an agent such as $Cl-SO_2R^3$ to provide the same or different 1-sulfonyl benzimidazole derivative. For example, a compound such as 1-isopropylsulfonyl-2-amino-6-($\alpha$-bromomethylenebenzyl)benzimidazole can be reacted with aqueous sodium hydroxide in acetone to give 2-amino-6-($\alpha$-bromomethylenebenzyl)benzimidazole sodium salt. The latter compound can be reacted with a sulfonic acid halide such as sec.-butylsulfonyl chloride to give the corresponding 1-sec.-butylsulfonyl olefinic benzimidazole. This general conversion is illustrated in the following scheme.

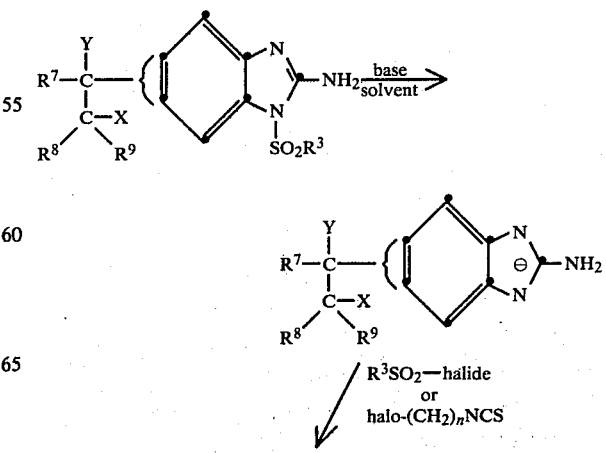

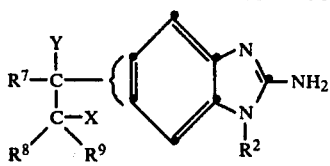

The 2-aminobenzimidazoles of the invention, compounds wherein $R^1$ is hydrogen, readily form pharmaceutically acceptable salts by reaction with mineral acids and organic acids. These salts are provided as a further embodiment of the invention. Organic acids commonly employed in the preparation of salts include acetic acid, butyric acid, para-toluenesulfonic acid, succinic acid, malonic acid and the like. Preferred salts are those formed with mineral acid such as hydrochloric acid, sulfuric acid, phosphoric acid and the like.

Table I below lists typical olefinic benzimidazoles embraced and provided by this invention. It will be noted that all of the olefinic benzimidazoles where one or both of $R^8$ and $R^9$ are other than halo are derived from the corresponding benzimidazole carbinol. The following recital is accordingly intended to exemplify the benzimidazole carbinols from which the listed olefinic benzimidazoles are derived.

In the Table, Column 1 recites the ring position of the olefinic moiety, i.e. whether the group is attached at the benzimidazole 5 or 6-position, or whether the compound depicted is a mixture of 5(6) isomers.

TABLE I

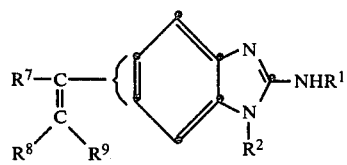

| 5 or 6 substituent | $R^1$ | $R^2$ | $R^7$ | $R^8$ | $R^9$ |
|---|---|---|---|---|---|
| 6 | H | SO₂CH₃ | phenyl- | H | Cl |
| 6 | H | SO₂CH₂CH₃ | phenyl- | CN | H |
| 6 | H | SO₂CH₂CH₂CH₃ | phenyl- | NO₂ | H |
| 6 | H | SO₂—cyclopropyl | 4-hydroxyphenyl- | Cl | Br |
| 6 | H | SO₂—cycloheptyl | CH₃ | H | SOCH₃ |
| 6 | H | SO₂—cyclopentyl | CH₃ | H | SO₂CH₂CH₃ |
| 6 | H | SO₂ (2-furyl) | H | SCH₃ | H |
| 5 | H | SO₂ (2-thienyl) | H | SCH₃ | H |
| 5 | H | SO₂—phenyl | 2-methylphenyl- | H | COOCH₃ |
| 5 | COCH₃ | SO₂ cycloheptyl | H | H | Cl |
| 5 | COCH₃ | SO₂—phenyl | CH₃ | H | Br |
| 5 | COCH₃ | SO₂N(CH₃)₂ | cyclopropylmethyl | H | F |
| 5 | COCH₂CH₃ | SO₂N(CH₃)CH₂CH₃ | cyclopentylmethyl | Br | Br |
| 5(6) | COCH₂CH₃ | SO₂ piperidino | 1-(cycloheptyl)-ethyl | Br | Cl |
| 6 | COCH₃ | SO₂ pyrrolidino | phenyl | NO₂ | H |
| 6 | H | SO₂ morpholino | 2-chlorophenyl | H | NO₂ |
| 6 | H | SO₂ isopropyl | 3-nitrophenyl | COOCH₃ | H |
| 6 | H | SO₂ isopropyl | phenyl | CH₂OH | H |
| 6 | H | SO₂ n-pentyl | phenyl | CH₂OCH₃ | H |
| 6 | H | SO₂ n-pentyl | phenyl | H | CN |
| 6 | H | thiazin-2-yl | 3-trifluoro-methylphenyl | H | COOCH₃ |
| 6 | H | thiazin-2-yl | phenyl | H | CONHCH₃ |
| 5 | H | thiazin-2-yl | H | H | CH₂NHCH₃ |
| 5(6) | H | thiazin-2-yl | CH₃ | CH₂NH₂ | H |
| 5 | H | thiazin-2-yl | cyclobutyl | CH₂N(CH₃)₂ | H |
| 5 | H | 4-methylthiazin-2-yl | cyclohexylmethyl | CON(CH₂CH₃)₂ | H |
| 5 | COCH(CH₃)₂ | 4-ethylthiazin-2-yl | phenyl | COOH | H |
| 6 | H | 4-methylthiazolin-2-yl | CH₃ | H | CH₂OCH₃ |
| 6 | H | SO₂CH₂CH₃ | isopropyl | H | CH₂OH |
| 6 | H | SO₂CH₂CH₂CH₃ | cyclobutylmethyl | H | CH₂N(CH₃)₂ |
| 6 | H | SO₂N(CH₃)₂ | phenyl | F | F |
| 6 | H | thiazolin-2-yl | 4-bromophenyl | H | SOCH₃ |
| 6 | H | SO₂ (2-thienyl) | H | H | CN |
| 5 | H | SO₂ (3-thienyl) | CH₂CH₃ | COOH | H |
| 5 | H | SO₂ (3-furyl) | 3-nitrophenyl | CONH₂ | H |
| 5 | H | SO₂CH₃ | CH₃ | CONHCH₃ | H |
| 5 | H | SO₂ n-pentyl | cyclobutyl | CH₂OH | H |
| 5 | H | SO₂ n-pentyl | cyclohexyl | CH₂NHCH₃ | H |
| 5 | H | SO₂ n-pentyl | n-heptyl | CONH₂ | H |
| 6 | COH | SO₂CH₃ | iso-heptyl | H | CH₂OCH₂CH₂N(CH₃)₂ |
| 6 | COCH₃ | thiazolin-2-yl | 4-methylhexyl | Br | Br |
| 5(6) | H | thiazolin-2-yl | phenyl | H | COCH₃ |

The olefinic benzimidazoles and benzimidazole carbinols provided by this invention have been shown to be effective in depressing and eliminating the growth of viruses. Accordingly, the compounds of this invention are valuable as antiviral agents and can be utilized in the control, treatment and prevention of any of a number of viral infections occurring in animals, including those caused by viruses such as Coxsackie (A9, A21, B5), echovirus (strains 1-4), mengo, rhinovirus (25 strains), Polio (types I, II and III) and related viruses. The antiviral activity of a number of the benzimidazoles comprehended by this invention has been evaluated in standard tests designed to measure such biological properties. One such test included the use of African green monkey kidney cells and Hela cells which were grown as described in U.S. Pat. No. 4,018,790. The cells were infected with Polio I virus, and the virus infected cells were overlaid with formulations containing various concentrations of a compound of this invention. Following incubation of the treated virus infected cells, the virus plaques which formed in those areas where the virus infected and reproduced in the cells were counted, and the plaque count was compared to the control count at each concentration level of test compound. The activity of test compound was then expressed as the concentration of compound (in μg/ml.) required to inhibit plaque formation by fifty percent (i.e. the $I_{50}$ value).

Table II presents the activity against Polio I virus for several of the olefinic benzimidazoles of the invention. The results presented in Table II are for 1-isopropylsulfonyl-2-amino-6-(α-substituted methylenebenzyl)benzimidazoles defined by the formula.

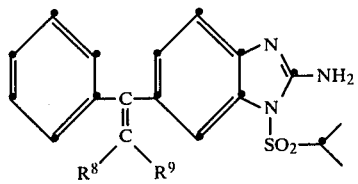

wherein $R^8$ and $R^9$ are as defined.

Columns I and II in Table II list, respectively, the groups defined in the above formula as $R^8$ and $R^9$. Column III records the concentration, in μg/ml., of each compound required to reduce the viral growth by fifty percent ($I_{50}$).

TABLE II

| Polio I Virus Inhibition ($I_{50}$) of olefinic benzimidazoles (mcg/ml.) | | |
|---|---|---|
| Column I $R^8$ | II $R^9$ | III $I_{50}$ |
| C≡N | H | 0.02 |
| H | C≡N | 0.17 |
| COOH | H | 12 |
| COOCH$_2$CH$_3$ | H | 0.08 |
| H | CONH$_2$ | 0.08 |
| CONH$_2$ | H | 0.01 |
| CH$_2$NH$_2$ | H | 25.0 |
| H | Cl | 6 |
| Cl | H | 0.01 |
| Cl | Cl | 0.35 |
| COOCH$_2$CH$_2$N(CH$_3$)$_2$ | H | 1.5 |
| Br | H | 0.02 |
| COOCH$_3$ | H | 0.01 |
| H | COOCH$_3$ | 0.08 |

Other olefinic benzimidazoles of this invention, with various $R^2$ substituents, have been similarly evaluated and have demonstrated excellent antiviral activity. For example, when 1-(thiazin-2-yl)-2-amino-6-(α-aminocarbonylmethylenebenzyl)benzimidazole was evaluated according to the procedure outlined above, it demonstrated and $I_{50}$ of about 0.35 to about 0.75 μg/ml. Such results demonstrate that the olefinic benzimidazoles provided herein are potent antiviral agents and can be used to combat infections caused by any of a number of viruses.

A number of the compounds of the invention have been evaluated in an in vitro tissue culture screen. This assay involved the growth of a sheet of cells on the bottom of a tissue culture plate. The cells were infected with a virus strain and overlayed with a uniform layer of nutrient agar. Filter paper discs impregnated with measured amounts of test compound were then applied on the surface of the agar. The plates were incubated at 37° C. and the cells are then fixed with Formalin and stained with a tetrachrome stain. Zones of antiviral activity attributable to the test compound are then read in millimeters. The morphology of protected cells is evaluated on a scale of 0 to 4, with 0 indicating completely damaged cells and 4 indicating normal cells.

Table III below presents the results of several compounds of the invention when evaluated in this in vitro assay. All compounds were analyzed at a concentration of 2000 mcg/ml. Zone sizes of cell protection are given in millimeters. Numbers in parenthesis following the zone sizes are morphology readings. Olefinic benzimidazoles wherein $R^8$ and $R^9$ are different were evaluated as a mixture of cis and trans isomers. Results reported as "-" indicate no activity observed at the dose level evaluated.

TABLE III

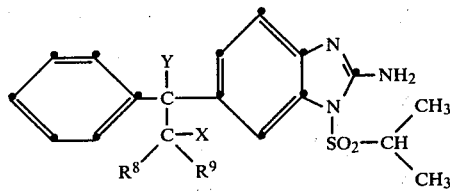

| | | | | Viral Strains | | | |
|---|---|---|---|---|---|---|---|
| Y | X | $R^8$ | $R^9$ | S. Forest | Polio | Ann Arbor | Coxsackie |
| OH | H | H | COOCH$_3$ | 13 (2) | 12 (2) | 20 (3) | 18 (2) |
| OH | H | H | CON(CH$_3$)$_2$ | — | 12 (3) | — | 13 (3) |
| OH | H | H | CONH$_2$ | — | — | 25 (1) | 17 (3) |
| OH | H | H | COOCH(CH$_3$)$_2$ | 20 (1) | 20 (3) | — | 20 (1) |
| = | | Cl | Cl | — | 15 (3) | 10 (2) | 16 (1) |

TABLE III-continued

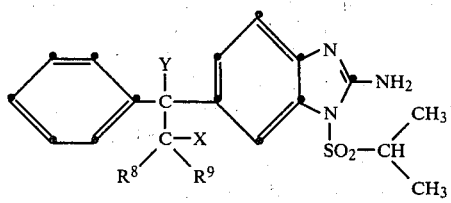

| Y | X | R⁸ | R⁹ | S. Forest | Polio | Ann Arbor | Coxsackie |
|---|---|---|---|---|---|---|---|
| = | | H | CH$_2$N(CH$_3$)$_2$(mixture) | — | 15 (2) | — | 10 (1) |
| = | | H | COOCH(CH$_3$)$_2$(mixture) | — | 20 (3) | — | 18 (1) |
| = | | H | COOCH$_2$CH$_2$CH$_3$(mixture) | — | 14 (1) | — | 12 (2) |
| = | | H | COOCH$_2$CH$_2$N(CH$_3$)$_2$(mixture) | — | 24 (1) | — | 24 (4) |
| = | | H | SCH$_3$(mixture) | 15 (3) | 25 (3) | — | — |
| = | | H | COOCH$_2$ cyclopropyl(mixture) | — | 17 (4) | — | 22 (2) |
| = | | H | SOCH$_3$(mixture) | — | 17 (4) | — | 12 (3) |
| = | | H | COOCH$_3$(mixture) | — | 35 (4) | — | 24 (3) |
| = | | H | COOH(mixture) | — | 15 (2) | — | 10 (2) |
| = | | H | COOCH$_2$CH$_3$(mixture) | — | 25 (1) | — | 23 (1) |

As already pointed out, an additional embodiment of this invention is a pharmaceutical formulation useful in the treatment and prophylactic control of viral infections in animals, especially humans. The formulations of this invention comprise a benzimidazole of the above general formula in combination with a pharmaceuticl diluent, excipient or carrier therefor. Preferred formulations have an olefinic benzimidazole as active ingredient. The formulations of this invention will contain about 0.5 to about 95% by weight of active ingredient. The compounds may be formulated for convenient oral administration by being mixed with solid diluents such as lactose, sorbitol, mannitol, starch, including potato starch and corn starch, amylopectin, cellulose derivatives, magnesium stearate, calcium stearate, polyethyleneglycol waxes, polyvinylpyrrolidone, and related diluents and excipients. Such formulations ideally are compressed into tablets for convenient oral administration. Alternatively, the formulations may be encapsulated in gelatine capsules or the like, or may be molded into a tablet suited to sublingual administration.

The compounds of the invention additionally are effective when administered rectally, and formulations suited to such administration ideally are prepared in the form of suppositories, which contain a benzimidazole of the invention admixed with a suitable neutral fat base or with a vegetable oil or paraffin oil.

Liquid preparations for oral administration may be prepared in the form of syrups or suspensions. Such formulations will contain about 0.5 to about 20 percent by weight of a compound of the invention, in combination with any of a number of suitable adjuvants such as sugar, ethanol, water, glycerol, propylene glycol and the like.

The benzimidazoles provided by this invention also may be administered parenterally to a subject suffering from a viral infection or in need of prophylactic treatment. For such administration, solutions may be prepared by dissolving a compound of the invention, particularly as an acid addition salt, in a suitable solvent such as isotonic saline, aqueous glucose, or the like. The solutions will contain from about 0.5 to about 80 percent by weight of a benzimidazole of the invention, preferably about 1 to about 20 percent by weight.

The compounds of the invention may also be formulated as a nasal spray or inhaler. Such formulations will contain ideally about 0.5 to about 10 percent by weight of a benzimidazole. Nasal sprays will generally contain about 0.5 to about 5 percent by weight of active ingredient, and will contain carriers such as non-ionic polyoxyethylated oils, alcohols such as ethanol, flavor agents such as menthol, and a propellant such as a polyhalogenated methane.

Yet another embodiment of this invention is a method of treating mammals suffering from a viral infection or in need of prophylactic control of viral infections. The method includes treatment of domesticated animals such as swine, cattle, horses and the like. The method comprises administering to a subject an antiviral amount of a benzimidazole defined by the above general formula. As hereinabove pointed out, the compounds can be suitably formulated for convenient administration by any of several routes, including the oral and parenteral routes. While the particular dosage of active compound may vary depending upon the particular benzimidazole selected, the route of administration, the specific virus to be treated or guarded against, the tolerance of the host, and various other parameters known to the medical community, the general rule is that a benzimidazole of this invention will be administered in an antiviral amount, which generally is a dose of about 0.1 to about 500 mg/kg. of animal body weight. A typical dose of active compound will more preferably be about 1 to about 300 mg/kg., and ideally about 10 to about 250 mg./kg. Such dosage can be administered about once each day, or in the case of more severe viral infections, the dosage can be administered from two to three times each day or more often as required. Such repeated dosing may be especially desirable when a compound is formulated as a nasal spray.

The following examples will serve to further illustrate specific embodiments of the invention.

EXAMPLE 1

1-Isopropylfonyl-2-amino-6-(α-hydroxy-α-cyanomethylbenzyl)benzimidazole.

A solution of 6.86 g. of acetonitrile in 200 ml. of tetrahydrofuran (THF) containing 115 ml. of a 1.6 molar solution of n-butyl lithium in THF was stirred at −70° C. in a dry ice-acetone bath. A solution of 7.0 g.

of 1-isopropylsulfonyl-2-amino-6-benzoylbenzimidazole in 300 ml. of THF was added dropwise to the reaction mixture over one hour. The reaction mixture then was stirred for three hours at −70° C., allowed to warm to room temperature, and then diluted by the dropwise addition of 200 ml. of water. The THF was removed from the reaction mixture by evaporation under reduced pressure, and the product was then extracted from the aqueous layer into ethyl acetate. The extracts were combined, dried, and the solvent was removed by evaporation under reduced pressure to afford 9.0 g. of a thick oil. The oil was purified by reverse phase high pressure liquid chromatography (45% methanol/water) to afford 6.0 g. of 1-isopropylsulfonyl-2-amino-6-(α-hydroxy-α-cyanomethylbenzyl)benzimidazole.

EXAMPLE 2

1-Isopropylsulfonyl-2-amino-6-(α-cyanomethylenebenzyl)benzimidazole.

A solution of 6.0 g. of 1-isopropylsulfonyl-2-amino-6-(α-hydroxy-α-cyanomethylbenzyl)benzimidazole (from Example 1) in 150 ml. of polyphosphoric acid was heated at 75° C. for ninety minutes. The reaction mixture was next added to 100 ml. of water containing 100 g. of ice, and the aqueous mixture was extracted several times with ethyl acetate. The extracts were combined, washed with water, dried, and the solvent was removed by evaporation under reduced pressure to provide 1.6 g. of the product as a solid. The solid thus formed was washed with diethyl ether and air dried to provide 1.6 g. of 1-isopropylsulfonyl-2-amino-6-(α-cyanomethylenebenzyl)benzimidazole.

EXAMPLE 3

Separation of cis and trans-1-isopropylsulfonyl-2-amino-6-(α-cyanomethylenebenzyl)benzimidazole.

The product from Example 2 was dissolved in 30 ml. of methanol and 5 ml. of dimethylsulfoxide and the mixture was warmed to 50° C. The solution was cooled to room temperature, whereupon 450 mg. of trans-1-isopropylsulfonyl-2-amino-6-(α-cyanomethylenebenzyl)benzimidazole crystallized. M.P. 209°–210° C.

Analysis calculated for $C_{19}H_{18}N_4O_2S$: Theory: C, 62.30; H, 4.92; N, 15.30. Found: C, 62.57; H, 4.92; N, 15.08.

The filtrate from above was diluted by the addition of 15 ml. of water and stored at room temperature for three hours. The crystalline solid which had formed was collected by filtration and dried to provide 700 mg. of cis-1-isopropylsulfonyl-2-amino-6-(α-cyanomethylenebenzyl)benzimidazole. M.P. 190°–193° C.

Analysis calculated for $C_{19}H_{18}N_4O_2S$ Theory: C, 62.30; H, 4.92; N, 15.30. Found: C, 62.36; H, 4.94; N, 15.00.

EXAMPLE 4

1-Isopropylsulfonyl-2-amino-6-(α-hydroxy-α-methoxycarbonylmethylbenzyl)benzimidazole.

To a stirred cold (−75° C.) solution of 42.2 ml. of hexamethyldisilazane in 100 ml. of THF was added dropwise over thirty minutes a solution of 125 ml. of 1.6 molar n-butyl lithium in THF, followed by the addition of 14.8 g. of methyl acetate dissolved in 25 ml. of THF. The temperature of the reaction mixture was maintained below −70° C. during the addition. Following the addition, the reaction mixture was stirred at −75° C. for thirty minutes, after which time a solution of 13.72 g. of 1-isopropylsulfonyl-2-amino-6-benzoylbenzimidazole in 750 ml. of THF was added dropwise over one hour. The reaction mixture was stirred at −75° C. for four hours, and then diluted with 150 ml. of water and 30 ml. of 1 N hydrochloric acid. The aqueous acid mixture was extracted several times with ethyl acetate. The extracts were combined, washed with water and with brine, dried, and the solvent was removed by evaporation under reduced pressure to provide 14.0 g. of the product as a white solid. The product was washed with diethyl ether and dried to give 14.0 g. of 1-isopropylsulfonyl-2-amino-6-(α-hydroxy-α-methoxycarbonylmethylbenzyl)benzimidazole. M.P. 147°–149° C.

Analysis calculated for $C_{20}H_{23}N_3O_5S$: Theory: C, 57.54; H, 5.55; N, 10.07. Found: C, 57.45; H, 5.55; N, 9.82.

EXAMPLES 5–10

Following the general procedure set forth in Example 4, the following (α-hydroxy-α-alkoxycarbonylmethylbenzyl)benzimidazoles were prepared by reacting a benzoylbenzimidazole with the appropriate alkylating agent.

1-Isopropylsulfonyl-2-amino-6-(α-hydroxy-α-isopropoxycarbonylmethylbenzyl)benzimidazole. M.P. 145°–146° C. Yield 3.75 g. (70%).

Analysis calcuated for $C_{22}H_{27}N_3O_5S$: Theory: C, 59.31; H, 6.11; N, 9.43. Found: C, 59.55; H, 6.32; N, 9.67.

1-Isopropylsulfonyl-2-amino-6-(α-hydroxy-α-tert.-butoxycarbonylmethylbenzyl)benzimidazole. Yield 16.5 g. (96%).

Analysis calculated for $C_{23}H_{29}N_3O_5S$: Theory: C, 60.11; H, 6.36; N, 9.14. Found: C, 59.21; H, 6.58; N, 8.22.

1-Isopropylsulfonyl-2-amino-6-(α-hydroxy-α-ethoxycarbonylmethylbenzyl)benzimidazole. Mass spec. $M^+$.

Theory: 431. Found: 431.

1-Isopropylsulfonyl-2-amino-6-(α-hydroxy-α-cyclopropylmethoxycarbonylmethylbenzyl)benzimidazole. Yield 5.63 g. (100%). Mass spec. $M^+$.

Theory: 457. Found: 457.

1-Isopropylsulfonyl-2-amino-6-(α-hydroxy-α-n-propoxycarbonylmethylbenzyl)benzimidazole.

1-Isopropylsulfonyl-2-amino-6-[α-hydroxy-α-(1-cyclopropylethoxy)carbonylmethylbenzyl]benzimidazole.

EXAMPLE 11

1-Isopropylsulfonyl-2-amino-6-(α-methoxycarbonylmethylenebenzyl)benzimidazole.

A solution of 6.0 g. of 1-isopropylsulfonyl-2-amino-6-(α-hydroxy-α-methoxycarbonylmethylbenzyl)benzimidazole (from Example 4) and 6.0 g. of p-toluenesulfonic acid in 150 ml. of chloroform was heated at reflux for three hours. The solution was cooled to room temperature and washed two times with saturated aqueous sodium bicarbonate solution, and two times with water. After drying the solution over sodium sulfate, the solvent was removed by evaporation under reduced pressure to provide 5.5 g. (96% yield) of 1-isopropylsulfonyl-2-amino-6-(α-methoxycarbonylmethylenebenzyl)benzimidazole. M.P. 160°–165° C.

Analysis calculated for $C_{20}H_{21}N_3O_4S$: Theory: C, 60.13; H, 5.30; N, 10.52. Found: C, 59.96; H, 5.12; N, 10.82.

Crystallization of 2.1 g. of the product from above from 50 ml. of methanol afforded 600 mg. of a first crop which was identified as trans-1-isopropylsulfonyl-2- amino-6-(α-methoxycarbonylmethylenebenzyl)benzimidazole. M.P. 199°–200° C.

Analysis, Found: C, 60.29; H, 5.41; N, 10.29.

EXAMPLES 12–16

By following the general procedure of Example 11, the appropriate (α-hydroxy-α-alkoxycarbonylmethylbenzyl)benzimidazole was dehydrated by reaction with p-toluenesulfonic acid in refluxing chloroform to provide the following (α-substituted methylenebenzyl)benzimidazoles.

1-Isopropylsulfonyl-2-amino-6-(α-n-propoxycarbonylmethylenebenzyl)benzimidazole. M.P. 165°–172° C. Yield 68%.

Analysis calculated for $C_{22}H_{25}N_3O_4S$: Theory: C, 61.81; H, 5.89; N, 9.83. Found: C, 61.89; H, 6.07; N, 9.55.

1-Isopropylsulfonyl-2-amino-6-(α-cyclopropylmethoxycarbonylmethylenebenzyl)benzimidazole. M.P. 200°–201° C. Yield 820 mg. (34%).

Analysis calculated for $C_{23}H_{26}N_3O_4S$: Theory: C, 62.85; H, 5.73; N, 9.56. Found: C, 62.63; H, 5.52; N, 9.42.

1-Isopropylsulfonyl-2-amino-6-(α-ethoxycarbonylmethylenebenzyl)benzimidazole. M.P. 59°–61° C. Yield 2.2 g. (76%).

Analysis calculated for $C_{21}H_{23}N_3O_4S$: Theory: C, 61.00; H, 5.61; N, 10.16. Found: C, 60.73; H, 5.63; N, 9.89.

1-Isopropylsulfonyl-2-amino-6-(α-isopropoxycarbonylmethylenebenzyl)benzimidazole. M.P. 148°–152° C. Yield 1.0 g. (66%).

Analysis calcuated for $C_{22}H_{25}N_3O_4S$: Theory: C, 61.81; H, 5.89; N, 9.83. Found: C, 61.60; H, 6.02; N, 9.53.

1-Isopropylsulfonyl-2-amino-6-[α-(1-cyclopropylethoxy)carbonylmethylenebenzyl]benzimidazole.

EXAMPLE 17

1-Isopropylsulfonyl-2-amino-6-(α-hydroxycarbonylmethylenebenzyl)benzimidazole.

A solution of 1.89 g. of 1-isopropylsulfonyl-2-amino-6-(α-hydroxy-α-tert.-butoxycarbonylmethylbenzyl)-benzimidazole (from Example 6) and 1.2 g. of p-toluenesulfonic acid in 100 ml. of chloroform was heated at reflux for two hours and then cooled to room temperature. The solution was extraced three times with aqueous sodium bicarbonate solution. The aqueous extracts were combined, washed with fresh chloroform and then neutralized to pH 7.0 by the addition of 1 N hydrochloric acid. The acidic solution next was extracted several times with ethyl acetate. The extracts were combined, washed with water and dried. Removal of the solvent by evaporation under reduced pressure provided 1-isopropylsulfonyl-2-amino-6-(α-hydroxycarbonylmethylenebenzyl)benzimidazole.

Analysis calculated for $C_{19}H_{19}N_3O_4S$: Theory: C, 59.21; H, 4.97; N, 10.90. Found: C, 59.20; H, 5.02; N, 10.67.

EXAMPLE 18

1-Isopropylsulfonyl-2-amino-6-(α-methoxycarbonylmethylenebenzyl)benzimidazole.

To a stirred solution of 0.77 g. of 1-isopropylsulfonyl-2-amino-6-(α-hydroxycarbonylmethylenebenzyl)benzimidazole (from Example 17) in 10 ml. of dimethylsulfoxide containing 0.1 g. of a fifty percent suspension of sodium hydride in mineral oil was added in one portion 0.3 g. of methyl iodide. The reaction mixture was stirred at room temperature for fifteen minutes, and then was diluted by the addition of 50 ml. of water. The aqueous mixture was extracted several times with ethyl acetate. The extracts were combined, washed with water, dried, and the solvent was removed by evaporation under reduced pressure to provide 1-isopropylsulfonyl-2-amino-6-(α-methoxycarbonylmethylenebenzyl)benzimidazole as a yellow solid.

Analysis calculated for $C_{20}H_{21}N_3O_4S$: Theory: C, 60.13; H, 5.30; N, 10.52. Found: C, 59.82; H, 5.41; N, 10.48.

EXAMPLE 19

1-Isopropylsulfonyl-2-amino-6-(α-chloromethylenebenzyl)benzimidazole.

To a stirred solution of 4.0 g. of 1-isopropylsulfonyl-2-amino-6-(α-methylenebenzyl)benzimidazole (from U.S. Pat. No. 4,118,742) in 100 ml. of tetrahydrofuran was added in one portion 1.56 g. of N-chlorosuccinimide. The reaction mixture was heated at reflux for two and one-half hours, and then cooled to room temperature. The reaction solvent was removed by evaporation under reduced pressure to provide the crude product as a gum. The gum was suspended in water, and then was extracted into chloroform. The chloroform extracts were combined, washed with fresh water, dried, and the solvent was removed by evaporation under reduced pressure. The product thus formed was dissolved in 50 ml. of diethyl ether, and after concentrating the volume of the mixture to about 25 ml., a white crystalline product precipitated and was identified as 1.5 g. of trans-1-isopropylsulfonyl-2-amino-6-(α-chloromethylenebenzyl)benzimidazole. M.P. 180°–181° C. Yield 34%.

Analysis calculated for $C_{18}H_{18}ClN_3O_2S$: Theory: C, 57.52; H, 4.83; N, 11.18. Found: C, 57.30; H, 4.87; N, 10.89.

Further concentration of the filtrate promoted crystallization of a second crop which was identified as 0.9 g. of cis-1-isopropylsulfonyl-2-amino-6-(α-chloromethylenebenzyl)benzimidazole. M.P. 158°–160° C. Yield 20%.

Analysis, Found: C, 57.53; H, 5.12; N, 11.04.

EXAMPLE 20

1-Isopropylsulfonyl-2-amino-6-(α-bromomethylenebenzyl)benzimidazole.

Following the general procedure set forth in Example 19, 5.0 g. of 1-isopropylsulfonyl-2-amino-6-(α-methylenebenzyl)benzimidazole was reacted with 2.9 g. of N-bromosuccinimide to provide 3.65 g. of the title compound. Yield 59%. Fractional crystallization of the product thus formed from diethyl ether afforded 1.0 g. of trans-1-isopropylsulfonyl-2-amino-6-(α-bromomethylenebenzyl)benzimidazole. M.P. 180°–182° C.

Analysis calculated for $C_{18}H_{18}BrN_3O_2S$: Theory: C, 51.44; H, 4.32; N, 10.00. Found: C, 51.24; H, 4.60; N, 9.90.

The crystallization also afforded 1.5 g. of the corresponding cis-isomer. M.P. 148°–149° C.

Analysis, found: C, 51.63; H, 4.59; N, 10.21.

EXAMPLE 21

1-Isopropylsulfonyl-2-amino-6-(α-dichloromethylenebenzyl)benzimidazole.

A solution of 1.7 g. of 1-isopropylsulfonyl-2-amino-6-(α-methylenebenzyl)benzimidazole and 1.4 g. of N-chlorosuccinimide in 50 ml. of tetrahydrofuran was heated at reflux for three hours. After cooling the reaction mixture to room temperature, the solvent was removed by evaporation under reduced pressure to provide the crude product as an oil. The oil was dissolved in 100 ml. of chloroform and washed three times with 50 ml. portions of water, dried, and the solvent was removed by evaporation. The product thus formed was crystallized from methanol and tetrahydrofuran to provide 800 mg. of 1-isopropylsulfonyl-2-amino-6-(α-dichloromethylenebenzyl)benzimidazole. M.P. 187°–188° C. Yield 39%.

Analysis calculated for $C_{18}H_{17}Cl_2N_3O_2S$: Theory: C, 52.69; H, 4.18; N, 10.24. Found: C, 52.56; H, 4.38; N, 10.03.

EXAMPLE 22

1-(Thiazin-2-yl)-2-amino-6-(α-hydroxy-α-aminocarbonylmethylbenzyl)benzimidazole.

To a stirred cold (−78° C.) solution of 37.5 ml. of 1.6 molar n-butyl lithium in 50 ml. of tetrahydrofuran was added dropwise over one hour a solution of 50 ml. of tetrahydrofuran containing 14.6 ml. of bistrimethylsilylacetamide. Following the addition, a solution of 4.0 g. of 1-(thiazin-2-yl)-2-amino-6-benzoylbenzimidazole in 300 ml. of tetrahydrofuran was added dropwise over one hour. The reaction mixture was stirred for an additional three hours, and then diluted with 300 ml. of water and allowed to warm to room temperature. The aqueous mixture was acidified with 1 N hydrochloric acid. The organic layer was separated and removed, and the aqueous acid layer was neutralized to pH 7.0 with 1 N sodium hydroxide. The aqueous mixture was extracted two times with ethyl acetate, and the combined extracts were washed with water and with brine, dried, and the solvent was removed by evaporation under reduced pressure to provide an oil. The oil was triturated with diethyl ether and the solid was dissolved in dilute hydrochloric acid. A precipitate formed and was filtered and dried to give 790 mg. of 1-(thiazin-2-yl)-2-amino-6-(α-hydroxy-α-aminocarbonylmethylbenzyl)benzimidazole hydrochloride.

Analysis calculated for $C_{18}H_{17}N_4OSCl$: Theory: C, 57.98; H, 4.60; N, 15.03; Cl, 9.51. Found: C, 57.90; H, 4.66; N, 15.01; Cl, 9.32.

The solvent was removed from the filtrate and the solid was identified as 1-(thiazin-2-yl)-2-amino-6-(α-hydroxy-α-aminocarbonylmethylbenzyl)benzimidazole.

Analysis calculated for $C_{18}H_{16}N_4OS$: Theory: C, 60.74; H, 5.35; N, 17.71. Found: C, 60.49; H, 5.50; N, 18.00.

EXAMPLE 23

1-Isopropylsulfonyl-2-amino-6-(α-hydroxy-α-aminocarbonylmethylbenzyl)benzimidazole.

A solution of 50 ml. of tetrahydrofuran containing 7.33 ml. of bistrimethylsilylacetamide (30 millimoles) and 18.75 ml. of a 1.6 Molar solution of n-butyl lithium (30 millimoles) was stirred at −78° C. for ten minutes. A solution of 1.03 g. (3 millimoles) of 1-isopropylsulfonyl-2-amino-6-benzoylbenzimidazole in 100 ml. of tetrahydrofuran was then added to the cold reaction mixture dropwise over one hour. The temperature of the reaction mixture was maintained at −78° C. throughout the addition, and the reaction mixture was stirred for four hours at −78° C. following complete addition of the benzoylbenzimidazole. The reaction mixture next was diluted with 75 ml. of water and 33 ml. of 1 N hydrochloric acid. The organic layer was separated and the aqueous acid layer was extracted several times with ethyl acetate. The organic layer and extracts were combined, washed with fresh water and dried. Removal of the solvent by evaporation under reduced pressure afforded a white solid product. Purification of the product by chromatography over silica gel afforded 1-isopropylsulfonyl-2-amino-6-(α-hydroxy-α-aminocarbonylmethylbenzyl)benzimidazole.

Analysis calculated for $C_{19}H_{22}N_4O_4S$: Theory: C, 56.70; H, 5.51; N, 13.92. Found: C, 56.68; H, 5.69; N, 13.70.

EXAMPLE 24

Following the general procedure of Example 23, N-methyl-N-trimethylsilylacetamide was reacted with 1-isopropylsulfonyl-2-amino-6-benzoylbenzimidazole in the presence of n-butyl lithium to provide 1-isopropylsulfonyl-2-amino-6-(α-hydroxy-α-methylaminocarbonylmethylbenzyl)benzimidazole. M.P. 92°–95° C.

EXAMPLE 25

1-Isopropylsulfonyl-2-amino-6-(α-hydroxy-α-dimethylaminocarbonylmethylbenzyl)benzimidazole.

To a cold (−75° C.) stirred solution of 62.5 ml. of a 1.6 molar solution of n-butyl lithium (100 millimoles) in 100 ml. of tetrahydrofuran containing 14.1 ml. (100 millimoles) of diisopropylamine was added dropwise over one-half hour a solution of 9.3 ml. (100 millimoles) of N,N-dimethylacetamide in 25 ml. of tetrahydrofuran. The temperature of the reaction mixture was maintained between −70° and −75° C. throughout the addition. Following complete addition of the dimethylacetamide, the reaction mixture was stirred at −75° C. for one-half hour. A solution of 6.86 g. (20 millimoles) of 1-isopropylsulfonyl-2-amino-6-benzoylbenzimidazole in 400 ml. of tetrahydrofuran was added dropwise to the cold reaction mixture at such rate that the temperature of the mixture did not rise above −70° C. Following the addition of the benzoylbenzimidazole, the reaction mixture was stirred at −75° C. for two hours. The reaction mixture was then warmed to room temperature, diluted with 200 ml. of water and 100 ml. of 1 N hydrochloric acid. The organic layer was separated, and the aqueous acid layer was separated several times with ethyl acetate. The organic layer and extracts were combined, washed with water and with brine, and then dried. Removal of the solvent by evaporation under reduced pressure afforded 5.8 g. of 1-isopropylsulfonyl-2-amino-6-(α-hydroxy-α-dimethylaminocarbonylmethylbenzyl)-benzimidazole. Yield 67.4%. M.P. 209°–210° C.

Analysis calculated for $C_{21}H_{26}N_4O_4S$: Theory: C, 58.59; H, 6.09; N, 13.01. Found: C, 58.47; H, 6.36; N, 12.83.

EXAMPLE 26

1-Isopropylsulfonyl-2-amino-6-(α-aminocarbonylmethylenebenzyl)benzimidazole.

A solution of 3.0 g. of p-toluenesulfonic acid and 3.0 g. of 1-isopropylsulfonyl-2-amino-6-(α-hydroxy-α-aminocarbonylmethylbenzyl)benzimidazole (prepared as described in Example 23) in 100 ml. of chloroform was heated at reflux for four hours. The reaction mixture then was cooled, washed with aqueous sodium bicarbonate solution and with water, dried, and the solvent was removed by evaporation under reduced pressure. Crystallization of the product thus formed from tetrahydrofuran afforded 1.1 g. of trans-1-isopropylsulfonyl-2-amino-6-(α-aminocarbonylmethylenebenzyl)benzimidazole, M.P. 218°–219° C. Yield 35%, and 1.0 g. of the corresponding cis-isomer, M.P. 211°-212° C., yield 32%.

Analysis calculated for $C_{19}H_{20}N_4O_3S$: Theory: C, 59.36; H, 5.24; N, 14.57. Found (trans): C, 59.14; H, 5.12; N, 14.40. Found (cis): C, 59.45; H, 5.21; N, 14.87.

EXAMPLES 27-28

Following the general procedure of Example 26, the appropriate (α-hydroxy-α-aminocarbonylmethylbenzyl)benzimidazole was dehydrated by reaction with p-toluenesulfonic acid to provide the following (α-aminocarbonylmethylenebenzyl)benzimidazoles.

1-Isopropylsulfonyl-2-amino-6-(α-methylaminocarbonylmethylenebenzyl)benzimidazole. M.P. 89°-90° C.

Analysis calculated for $C_{20}H_{22}N_4O_3S$: Theory: C, 60.28; H, 5.57; N, 14.06. Found: C, 59.52; H, 5.05; N, 12.96.

1-Isopropylsulfonyl-2-amino-6-(α-dimethylaminocarbonylmethylenebenzyl)benzimidazole.

M.P. (trans): 194°-195° C. Yield 24%.

M.P. (cis): 169°-172° C. Yield 20%.

Analysis calculated for $C_{21}H_{24}N_4O_3S$: Theory: C, 61.15; H, 5.86; N, 13.58. Found (trans): C, 60.38; H, 4.56; N, 13.11. Found (cis): C, 61.33; H, 5.78; N, 13.37.

EXAMPLE 29

1-(Thiazin-2-yl)-2-amino-6-(α-aminocarbonylmethylenebenzyl)benzimidazole

A solution of 300 mg. of 1-(thiazin-2-yl)-2-amino-6-(α-hydroxy-α-aminocarbonylmethylbenzyl)benzimidazole (from Example 22) in 4 ml. of 97% formic acid was allowed to stand at room temperature for twenty-four hours. The reaction mixture was then neutralized by the addition of saturated aqueous sodium bicarbonate, and the product was extracted therefrom into chloroform. The chloroform extracts were combined and concentrated in volume under reduced pressure to provide an oil. The oil was purified by chromatography over silica gel (LOBAR, Merck) eluting with chloroform, methanol, acetic acid (70:10:20 v/v/v). Fractions containing the major components were combined and the solvent was removed by evaporation under reduced pressure to provide an oil. The oil was dissolved in water and added to aqueous sodium bicarbonate, whereupon a white precipitate formed. The precipitate was collected by filtration and dried to give 130 mg. of 1-(thiazin-2-yl)-2-amino-6-(α-aminocarbonylmethylenebenzyl)benzimidazole. Mass spec. M+ Theory 377. Found 377. UV ($CH_3OH$) $\lambda_{210}$ (E35,500) $\lambda_{250}$ (E 23,500); $\lambda_{310}$ (E 10,250).

Analysis calculated for $C_{20}H_{19}N_5OS$: Theory: C, 63.64; H, 5.07; N, 18.55. Found: C, 62.59; H, 5.01; N, 17.79.

EXAMPLE 30

1-Isopropylsulfonyl-2-amino-6-[α-(2-aminoethylenebenzyl)]benzimidazole.

To a stirred solution of 2.0 g. of 1-isopropylsulfonyl-2-amino-5-(α-hydroxy-α-aminocarbonylmethylbenzyl)benzimidazole in 200 ml. of tetrahydrofuran was added dropwise over ten minutes 2.5 ml. of boranemethyl sulfide complex in 25 ml. of tetrahydrofuran. The reaction mixture was then heated at reflux under a nitrogen atmosphere for three hours. The reaction mixture then was cooled to room temperature and diluted by the dropwise addition of 25 ml. of 1 N hydrochloric acid, followed by the addition in one portion of 100 ml. of 3 N hydrochloric acid. The acidic reaction mixture was washed two times with 50 ml. portions of ethyl acetate and once with diethyl ether. The aqueous acid layer then was neutralized by the addition of aqueous sodium hydroxide. The product precipitated out of solution and the solvent was decanted. The solid precipitate was dissolved in 12 N hydrochloric acid, and the solution was heated at 100° C. for three hours. The solution next was cooled to room temperature, and the pH was adjusted to 7.0 with ammonium hydroxide. The product precipitated from the solution as a white solid which was then collected by filtration. Chromatography over silica gel of the product thus formed effected separation of cis and trans isomers to provide 100 mg. of trans-1-isopropylsulfonyl-2-amino-6-[α-(2-aminoethylenebenzyl)]benzimidazole, M.P. 184°-186° C.

Analysis calculated for $C_{19}H_{22}N_4O_2S$: Theory: C, 61.60; H, 5.99; N, 15.12. Found: C, 61.90; H, 6.15; N, 15.33. and 150 mg. of the corresponding cis-isomer, M.P. 140°-50° C.

EXAMPLE 31

Following the procedure of Example 30, 1-isopropylsulfonyl-2-amino-6-(α-hydroxy-α-dimethylaminocarbonylmethylbenzyl)benzimidazole was reacted with borane-methyl sulfide complex to provide, after purification, 1-isopropylsulfonyl-2-amino-6-[α-(2-dimethylaminoethylenebenzyl)]benzimidazole. M.P. 140°-145° C. Yield 35%.

Analysis calculated for $C_{21}H_{26}N_4O_2S$: Theory: C, 63.29; H, 6.58; N, 14.06. Found: C, 63.25; H, 6.78; N, 13.84.

EXAMPLE 32

1-Isopropylsulfonyl-2-amino-6-(α-hydroxy-α-methylsulfinylmethylbenzyl)benzimidazole.

Lithium methyl sulfinyl carbanion was prepared by reacting 37 ml. of a 1.6 M solution of n-butyl lithium in tetrahydrofuran with 5 ml. of dimethyl sulfoxide dissolved in 70 ml. of tetrahydrofuran. After stirring the reaction mixture under nitrogen for thirty minutes at 0°-5° C., a mixture of 4.0 g. of 1-isopropylsulfonyl-2-amino-6-benzoylbenzimidazole in 60 ml. of tetrahydrofuran was added in one portion. The reaction mixture was stirred for one hour at 0° C., and then was warmed to room temperature and stirred for an additional twelve hours at 24° C., followed by thirty-six hours of stirring at 50° C. The reaction mixture next was diluted with 100 ml. of water, and the organic solvent was removed by evaporation under reduced pressure. The aqueous mixture was acidified to pH 2 with 1 N hydrochloric acid, and then filtered. The filtrate was neutralized with sodium carbonate, and the product was extracted therefrom into ethyl acetate. The extracts were combined and the solvent was removed by evaporation under reduced pressure to provide 1-isopropylsulfonyl-2-amino-6-(α-hydroxy-α-methylsulfinylmethylbenzyl)-benzimidazole.

Analysis calculated for $C_{19}H_{23}N_3O_4S_2$: Theory: C, 56.16; H, 5.46; N, 9.97. Found: C, 53.76; H, 5.57; N, 9.24.

EXAMPLE 33

1-Isopropylsulfonyl-2-amino-6-(α-methylsulfinylmethylenebenzyl)benzimidazole.

A solution of 120 mg. of p-toluenesulfonic acid monohydrate and 240 mg. of 1-isopropylsulfonyl-2-amino-6-(α-hydroxy-α-methylsulfinylmethylbenzyl)benzimidazole from Example 32 in 50 ml. of chloroform was heated at reflux for sixteen hours. The reaction mixture was then cooled, washed with water, dried, and the solvent was removed by evaporation under reduced pressure. The crude product thus formed was crystallized from methanol to afford 30 mg. of 1-isopropylsulfonyl-2-amino-6-(α-methylsulfinylmethylenebenzyl)-benzimidazole. Yield 13%.

Analysis calculated for $C_{19}H_{21}N_3O_3S_2$: Theory: C, 56.66; H, 5.25; N, 10.41. Found: C, 56.52; H, 5.45; N, 10.38.

EXAMPLE 34

1-Isopropylsulfonyl-2-amino-6-(α-hydroxy-α-methylthiomethylbenzyl)benzimidazole

To a cold (0° C.) stirred solution of 62.5 ml. of 1.6 M n-butyllithium in THF were added dropwise 11.6 g. of tetramethylethylenediamine. The reaction mixture was stirred at 10° C. while 6.0 g. of dimethylsulfide were added in one portion. The reaction mixture was warmed to room temperature and stirred for four hours, and then was cooled to −50° C. in an acetone/dry ice bath. To the cold stirred reaction mixture were added portionwise a suspension of 6.8 g. of 1-isopropylsulfonyl-2-amino-6-benzoylbenzimidazole in 200 ml. of THF. Following complete addition of the benzoylbenzimidazole, the reaction mixture was warmed to 24° C. and stirred for sixteen hours. The reaction mixture than was diluted with 50 ml. of methanol and 50 ml. of water. The organic solvents were removed by evaporation under reduced pressure, and the aqueous mixture was diluted with 100 ml. of saturated ammonium chloride, and then extracted several times with chloroform. The extracts were combined, washed with water and brine, dried, and the solvent was removed by evaporation under reduced pressure to give 6.2 g. of 1-isopropylsulfonyl-2-amino-6-(α-hydroxy-α-methylthiomethylbenzyl)benzimidazole. Yield 76%.

EXAMPLE 35

1-Isopropylsulfonyl-2-amino-6-(α-hydroxy-α-methylthiomethylbenzyl)benzimidazole from Example 34 was dehydrated by the method of Example 33 to provide 1-isopropylsulfonyl-2-amino-6-(α-methylthiomethylenebenzyl)benzimidazole.

Analysis calculated for $C_{19}H_{21}N_3O_2S_2$: Theory: C, 58.89; H, 5.46; N, 10.84. Found: C, 58.61; H, 5.50; N, 10.64.

EXAMPLE 36

1-Dimethylaminosulfonyl-2-amino-6-(α-bromomethylenebenzyl)benzimidazole.

To a stirred solution of 228 mg. of 1-dimethylaminosulfonyl-2-amino-6-(α-methylenebenzyl)benzimidazole (U.S. Pat. No. 4,118,742) in 10 ml. of tetrahydrofuran was added in one portion 238 mg. of a mixture of 1,5-diazabicyclo[5.4.0]undec-5-ene (i.e. commercial DBU), bromine and hydrobromic acid. The reaction mixture was stirred for ten minutes, and then the solvent was removed by evaporation under reduced pressure. The residue was dissolved in 30 ml. of chloroform and washed with 25 ml. of water. The organic layer was separated, dried, and the solvent was removed by evaporation to provide 241 mg. of a white solid. The solid was crystallized from 20 ml. of ethyl acetate to afford 89 mg. of 1-dimethylaminosulfonyl-2-amino-6-(α-bromomethylenebenzyl)benzimidazole.

Analysis calculated for $C_{17}H_{17}BrN_4O_2S$: Theory: C, 48.46; H, 4.07; N, 13.30; Br, 18.97. Found: C, 48.36; H, 4.05; N, 13.86; Br, 19.29.

EXAMPLE 37

1-Dimethylaminosulfonyl-2-amino-6-(α-chloromethylenebenzyl)benzimidazole.

A solution of 456 mg. of 1-dimethylaminosulfonyl-2-amino-6-(α-methylenebenzyl)benzimidazole in 20 ml. of tetrahydrofuran containing 176 mg. N-chlorosuccinimide was heated at reflux for two hours and then stirred at room temperature for an additional three hours. The solvent was then removed by evaporation under reduced pressure to provide an oil, which was next dissolved in chloroform and washed with water. The organic layer was separated, dried, and the solvent was removed to afford 404 mg. of the product as a solid. The solid was crystallized from 35 ml. of ethyl acetate to give 196 mg. of 1-dimethylaminosulfonyl-2-amino-6-(α-chloromethylenebenzyl)benzimidazole. M.P. 207°–215° C. Yield 23%.

Analysis calculated for $C_{17}H_{17}ClN_4O_2S$: Theory: C, 54.18; H, 4.55; N, 14.87; Cl, 9.41. Found: C, 54.28; H, 4.52; N, 14.86; Cl, 9.37.

EXAMPLE 38

1-(Thiazin-2-yl)-2-amino-6-(α-chloromethylenebenzyl)benzimidazole.

A solution of 500 mg. of 1-(thiazin-2-yl)-2-amino-6-(α-methylenebenzyl)benzimidazole in 50 ml. of tetrahydrofuran containing 250 mg. of N-chlorosuccinimide was stirred at room temperature for sixteen hours. The reaction mixture was filtered, and the filtrate was diluted with water and then concentrated to a volume of about 25 ml. The precipitate which formed was collected by filtration, dried, and identified as 140 mg. of 1-(thiazin-2-yl)-2-amino-6-(α-chloromethylenebenzyl)-benzimidazole.

Analysis calculated for $C_{19}H_{17}ClN_4S$: Theory: C, 61.86; H, 4.65; N, 15.19; Cl, 9.61. Found: C, 61.16; H, 4.89; N, 14.59; Cl, 10.29.

Additional product crystallized from the filtrate and was collected by filtration; 180 mg. Total yield 64%.

EXAMPLE 39

1-Isopropylsulfonyl-2-amino-6-[α-(2-N,N-dimethylaminoethoxycarbonylmethylene)benzyl]benzimidazole.

A solution of 192 mg. of 1-isopropylsulfonyl-2-amino-6-(α-hydroxycarbonylmethylenebenzyl)benzimidazole (from Example 17) in 25 ml. of N,N-dimethylformamide containing 55 mg. of a fifty percent mineral oil dispersion of sodium hydride and 120 mg. of 2-(N,N-dimethylamino)ethyl bromide was stirred at room temperature for one-half hour. The reaction solvent was concentrated by evaporation under reduced pressure, and the residue was then dissolved in 50 ml. of 1 N hydrochloric acid. The acidic solution was washed two times with 25 ml. portions of chloroform, and then neutralized by the addition of aqueous sodium bicarbonate. The aqueous solution was extracted several times with ethyl acetate, and the extracts were combined, washed with water and dried. Removal of the solvent by evaporation under reduced pressure provided a solid, which after trituration with diethyl ether and drying, was identified as 70 mg. of 1-isopropylsulfonyl-2-amino-6-[α-(2-N,N-dimethylaminoethoxycarbonylmethylene)-benzyl]benzimidazole. M.P. 112°–114° C. Yield 31%.

Analysis calculated for $C_{23}H_{28}N_4O_4S$: Theory: C, 60.54; H, 6.14; N, 12.27. Found: C, 60.28; H, 6.24; N, 11.80.

EXAMPLE 40

1-Isopropylsulfonyl-2-acetamido-6-(α-cyanomethylenebenzyl)benzimidazole

A solution of 500 mg. (1.4 millimole) of 1-isopropylsulfonyl-2-amino-6-(α-cyanomethylenebenzyl)benzimidazole (prepared as described in Example 2) in 5 ml. of acetic anhydride was stirred at ambient temperature for four hours. The reaction mixture was poured into 50 ml. of water and the aqueous mixture was stirred at room temperature for sixteen hours. The aqueous reaction mixture was extracted several times with methyl isobutyl ketone, and the organic extracts were combined and dried. The organic solvent was removed by evaporation under reduced pressure to provide 460 mg. of 1-isopropylsulfonyl-2-acetamido-6-(α-cyanomethylenebenzyl)benzimidazole.

Analysis calculated for $C_{21}H_{20}N_4O_3S$: Theory; C, 61.75; H, 4.94; N, 13.72. Found: C, 61.56; H, 5.25; N, 13.61.

EXAMPLE 41

1-(Thiazin-2-yl)-2-amino-6-(α-dichloromethylenebenzyl)benzimidazole.

A solution of 1.0 g of 1-(thiazin-2-yl)-2-amino-6-(α-methylenebenzyl)benzimidazole in 50 ml. of tetrahydrofuran containing 500 mg. of N-chlorosuccinimide stood at room temperature for twelve hours. A small amount of solid precipitate was removed by filtration. An additional 500 mg. portion of N-chlorosuccinimide was added to the filtrate and the solution was stirred for six hours at room temperature. Another 500 mg. portion of N-chlorosuccinimide was then added to the reaction mixture and stirring was continued for twelve hours. The white precipitate which had formed was collected by filtration and air dried to give 640 mg. (57%) of 1-(thiazin-2-yl)-2-amino-6-(α-dichloromethylenebenzyl)benzimidazole hydrochloride. M.P. 214°–217° C.

Analysis calculated for $C_{19}H_{17}N_4SCl_3$: Theory: C, 52.13; H, 3.45; N, 12.80. Found: C, 52.15; H, 3.69; N, 13.05.

EXAMPLE 42

1-Isopropylsulfonyl-2-amino-6-[α(2-hydroxyethylene)benzyl]benzimidazole.

(A) A solution of 1.0 g. of 1-isopropylsulfonyl-2-amino-6-benzoylbenzimidazole in 100 ml. of tetrahydrofuran and 25 ml. of 1.1 molar vinyl magnesium bromide was stirred under a nitrogen atmosphere for two hours at room temperature. The reaction mixture was then added to 700 ml. of pH 7.0 buffer solution. The aqueous mixture was adjusted to pH 8 with 1 N hydrochloric acid, and extracted several times with ethyl acetate. The extracts were combined, washed with water, dried, and the solvent was removed by evaporation under reduced pressure to afford a yellow foam. The foam was purified by high pressure liquid chromatography to provide 320 mg. of 1-isopropylsulfonyl-2-amino-6-(α-hydroxy-α-ethylene)benzylbenzimidazole. M.P. 133°–134° C.

Analysis calculated for $C_{19}H_{21}N_3O_3S$: Theory: C, 61.45; H, 5.66; N, 11.32. Found: C, 61.10; H, 5.75; N, 11.11.

(B) A solution of 50 mg. of the alcohol thus formed in 2 ml. of dioxane containing 2 ml. of 1 N hydrochloric acid was stirred at room temperature for sixteen hours. The reaction mixture was lyophilized to provide a white solid. The solid was chromatographed to provide 1-isopropylsulfonyl-2-amino-6-[α-(2-hydroxyethylene)-benzyl]benzimidazole hydrochloride.

Analysis calculated for $C_{19}H_{21}N_3O_3S$: Theory: C, 55.95; H, 5.40; N, 10.30; Cl, 8.70. Found: C, 56.62; H, 4.91; N, 9.57; Cl, 8.37.

EXAMPLE 43

2-Amino-6-(α-ethylenebenzyl)benzimidazole

A slurry of 4.6 g. of 1-isopropylsulfonyl-2-amino-6-(α-ethylenebenzyl)benzimidazole in 50 ml. of acetone and 50 ml. of water containing 16 ml. of 1 N sodium hydroxide was heated at 100° C. until all of the acetone had boiled off. The reaction mixture was cooled to room temperature and then filtered. The precipitate was washed with water and air dried to give 2.75 g. (74%) of 2-amino-6-(α-ethylenebenzyl)benzimidazole.

Analysis calculated for $C_{16}H_{15}N_3$: Theory: C, 77.08; H, 6.06; N, 16.85. Found: C, 77.33; H, 6.12; N, 16.57.

EXAMPLE 44

1-Phenylsulfonyl-2-amino-6-(α-chloromethylenebenzyl)benzimidazole.

1-Isopropylsulfonyl-2-amino-6-(α-chloromethylenebenzyl)benzimidazole is reacted with sodium hydroxide in acetone and water by the method of Example 43 to give 2-amino-6-(α-chloromethylenebenzyl)benzimidazole. The latter compound is reacted with phenylsulfonyl chloride and sodium hydroxide in dichloromethane to give 1-phenylsulfonyl-2-amino-6-(α-chloromethylenebenzyl)benzimidazole.

EXAMPLE 45

1-(Thiazolin-2-yl)-2-amino-6-(α-bromomethylenebenzyl)benzimidazole

To a stirred solution of 1.6 g. (5 mM) of 1-(thiazolin-2-yl)-2-amino-6-(α-methylenebenzyl)benzimidazole in 150 ml. of tetrahydrofuran were added in one portion 900 mg. (0.5 mM) of N-bromosuccinimide. The reaction mixture was stirred at room temperature for seventy-two hours, and then was concentrated to a volume of about 10 ml. by evaporation of the solvent under reduced pressure. The reaction mixture was diluted with 20 ml. of water, and the crystalline precipitate that formed was collected by filtration and identified as 600 mg. of 1-(thiazolin-2-yl)-2-amino-6-(α-bromomethylenebenzyl)benzimidazole. M.P. 197°–199° C. Yield 30%.

Analysis calculated for $C_{18}H_{15}BrN_4S$: Theory: C, 53.91; H, 3.74; N, 13.08. Found: C, 54.14; H, 3.79; N, 14.03.

EXAMPLE 46

1-(Thiazolin-2-yl)-2-amino-6-(α-aminocarbonylmethylenebenzyl)benzimidazole

To a cold (−70° C.) stirred solution of 122 g. of bis(-trimethylsilyl)acetamide in 500 ml. of tetrahydrofuran (THF) were added dropwise 250 ml. of n-butyllithium, followed by the addition portionwise of a slurry of 32.2 g. of 1-(thiazolin-2-yl)-2-amino-6-benzoylbenzimidazole in 1500 ml. of THF. The reaction mixture was stirred at −70° C. for six hours following the addition. The reaction mixture was then added to 2 liters of cold water, and the organic layer was separated, dried, and the solvent was removed by evaporation under reduced pressure to 33.27 g. of 1-(thiazolin-2-yl)-2-amino-6-(α- trimethylsilyloxy-α-aminocarbonylmethylbenzyl)benzimidazole. M.P. 242°–243° C.

Analysis calculated for $C_{22}H_{27}N_5O_2SSi$: Theory: C, 58.40; H, 5.78; N, 15.39; O, 6.86. Found: C, 58.25; H, 6.00; N, 15.44; O, 7.05.

A solution of 9.06 g. of the compound from above in 50 ml. of formic acid was heated at about 80° C. for one hour. The reaction mixture was then added to 50 ml. of water, and the aqueous mixture was made alkaline with 1 N sodium hydroxide. The precipitate that formed was collected by filtration and recrystallized from methyl ethyl ketone to give 6.15 g. of 1-(thiazolin-2-yl)-2-amino-6-(α-aminocarbonylmethylenebenzyl)benzimidazole. M.P. 228° C. Yield 84.6%.

Analysis calculated for $C_{19}H_{17}N_5OS$: Theory: C, 62.79; H, 4.81; N, 19.06; O, 4.51. Found: C, 62.79; H, 4.71; N, 19.27; O, 4.40.

EXAMPLE 47

1-(Thiazolin-2-yl)-2-amino-6-(α-aminocarbonylmethylenebenzyl)benzimidazole methanesulfonate A suspension containing 2.0 g. of 1-(thiazolin-2-yl)-2-amino-6-(α-aminocarbonylmethylenebenzyl)benzimidazole (from Example 46) and 1.0 g. of methanesulfonic acid in 200 ml. of isopropyl alcohol was stirred for two hours at 24° C. The reaction mixture was filtered and the solids were washed with fresh isopropyl alcohol and hexane, and then dried to give 6.5 g. of 1-(thiazolin-2-yl)-2-amino-6-(α-aminocarbonylmethylenebenzyl)-benzimidazole methanesulfonate. M.P. 235°–237° C.

Analysis calculated for $C_{20}H_{21}N_5O_4S_2$: Theory: C, 52.03; H, 4.52; N, 15.00; O, 13.69; S, 13.78. Found: C, 52.27; H, 4.61; N, 15.24; O, 13.93; S, 13.95.

EXAMPLE 48

| Preparation of 250 mg. Tablets | |
|---|---|
| 1-Dimethylaminosulfonyl-2-amino-6-[(α-ethoxycarbonylmethylene)cyclobutylmethyl]-benzimidazole | 250 mg. |
| Lactose | 200 mg. |
| Corn Starch | 300 mg. |
| Corn Starch Paste | 50 mg. |
| Calcium Stearate | 5 mg. |
| Dicalcium Phosphate | 45 mg. |

The olefinic benzimidazole, corn starch, lactose and dicalcium phosphate are uniformly blended. The corn starch paste is prepared as a 10 percent aqueous paste and is blended into the mixture to uniformity. The mixture is blended with the calcium stearate and then compressed into a tablet. Such tablets are administered at the rate of 1 to about 6 tablets per day to a subject weighing about 70 kg. and suffering from a viral infection such as influenza.

EXAMPLE 49

| Preparation for Suppositories | |
|---|---|
| 1-Isopropylsulfonyl-2-acetamido-5-(α-dibromomethylenebenzyl)benzimidazole | 500 mg. |
| Theobromo oil | 1500 mg. |

The above ingredients are blended to uniformity at a temperature of about 60° C. and then cooled in a tapered mold. Such suppository can be administered to a human suffering from a viral infection caused by Polio I virus or the like.

EXAMPLE 50

| Preparation for oral suspension | |
|---|---|
| 1-Ethylsulfonyl-2-amino-6-(α-aminocarbonylmethylenebenzyl)benzimidazole (as the hydrochloride salt) | 500 mg. |
| Sorbitol solution (70% N.F.) | 40 mg. |
| Sodium benzoate | 150 mg. |
| Lactose | 10 mg. |
| Cherry flavor | 50 mg. |
| Ethanol | 100 ml. |

The above ingredients are combined such that each ml. of syrup contains 5 mg. of active ingredient. Administration of about 5 to about 20 ml. of the syrup each day will protect a human subject from viral infections manifested as common colds.

EXAMPLE 51

| Intranasal Formulation | |
|---|---|
| | Percent by weight |
| 1-Isopropylsulfonyl-2-amino-6-[(α-bromomethylene)-4-methoxybenzyl]benzimidazole | 1.0 |
| Antarox (non-ionic polyoxyethylated fixed oil, GAF Corp.) | 38.5 |
| Ethanol | 10.0 |
| Freon 11 (trichloromonofluoromethane) | 25.0 |
| Freon 12 (dichlorodifluoromethane) | 25.0 |
| Menthol | 0.5 |

The olefinic benzimidazole is added to the Antarox at about 70°–80° C. and the mixture is stirred until a solution is formed. The solution is cooled and diluted with a mixture of the menthol in the ethanol. The resulting solution is placed in an aerosol container and chilled to 0° C., and the Freon propellants are added and the aerosol container is sealed with a valve.

We claim:

1. A compound of the formula wherein:
$R^1$ is hydrogen or $C_1$–$C_4$ alkanoyl;
$R^2$ is hydrogen, —$SO_2R^3$ or a group of the formula in which:
$R^3$ is $C_1$–$C_5$ alkyl, $C_3$–$C_7$ cycloalkyl, phenyl, furyl, thienyl, or $R^5R^6N$, wherein $R^5$ and $R^6$ independently are $C_1$–$C_3$ alkyl, or taken together with the nitrogen to which they are attached are pyrrolidino, piperidino or morpholino;

$R^4$ is hydrogen, $C_1$–$C_3$ alkyl, phenyl, or benzyl; and n is 2 or 3;

$R^7$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, phenyl, or phenyl substituted with one group selected from hydroxy, halo, $C_1$–$C_4$ alkoxy, nitro or trifluoromethyl;

X is hydrogen and Y is hydroxy, or together X and Y form a bond;

$R^8$ and $R^9$ independently are hydrogen, halo, cyano, nitro, $$\overset{(O)_m}{\underset{}{S}}C_1\text{–}C_4$$

alkyl, $CH_2R^{10}$, $COR^{10}$, phenyl, or phenyl substituted with one group selected from hydroxy, halo, $C_1$–$C_4$ alkoxy, nitro or trifluoromethyl;

m is 0, 1 or 2;

$R^{10}$ is hydroxy, $C_1$–$C_4$ alkoxy, $C_1$–$C_4$ alkanoyloxy, halo, $C_3$–$C_6$ cycloalkyl-$C_1$–$C_4$ alkoxy, or $(O\text{–}C_1\text{–}C_4 \text{ alkyl})_y NR^{11}R^{12}$ where y is 0 or 1, and $R^{11}$ and $R^{12}$ independently are hydrogen or $C_1$–$C_4$ alkyl;

provided that one and only one of $R^8$ and $R^9$ is hydrogen, except when either of $R^8$ or $R^9$ is halo, the other may be halo, and when Y is hydroxy, $R^8$ and $R^9$ are other than halo; and the pharmaceutically acceptable acid addition salts thereof.

2. The compound of claim 1 wherein X and Y together are a bond.

3. The compound of claim 2 wherein $R^2$ is 2-thiazolinyl or 2-thiazinyl.

4. The compounds of claim 3 wherein $R^1$ is hydrogen and $R^7$ is phenyl.

5. The compound of claim 4 wherein one of $R^8$ and $R^9$ independently is hydrogen and the other is halo, cyano, or $COR^{10}$ wherein $R^{10}$ is $C_1$–$C_4$ alkoxy, or $(O\text{–}C_1\text{–}C_4 \text{ alkyl})_y NR^{11}R^{12}$.

6. The compound of claim 5 wherein one of $R^8$ and $R^9$ is halo.

7. The compound of claim 6, said compound being 1-(thiazin-2-yl)-2-amino-6-(α-chloromethylenebenzyl)benzimidazole.

8. The compound of claim 6, said compound being 1-(thiazolin-2-yl)-2-amino-6-(α-bromomethylenebenzyl)benzimidazole.

9. The compound of claim 5, said compound being 1-(thiazin-2-yl)-2-amino-6-(α-aminocarbonylmethylenebenzyl)benzimidazole.

10. The compound of claim 5, said compound being 1-(thiazolin-2-yl)-2-amino-6-(α-aminocarbonylmethylenebenzyl)benzimidazole.

11. The compound of claim 2 wherein $R^2$ is $SO_2R^3$.

12. The compound of claim 11 wherein $R^3$ is $C_1$–$C_5$ alkyl or $R^5R^6N$ wherein $R^5$ and $R^6$ independently are $C_1$–$C_3$ alkyl.

13. The compound of claim 12 wherein $R^7$ is phenyl.

14. The compound of claim 13 wherein one of $R^8$ and $R^9$ independently is hydrogen and the other is halo, cyano, or $COR^{10}$ wherein $R^{10}$ is $C_1$–$C_4$ alkoxy, $C_3$–$C_6$ cycloalkyl-$C_1$–$C_4$ alkoxy, or $(O\text{–}C_1\text{–}C_4 \text{ alkyl})_y NR^{11}R^{12}$.

15. The compound of claim 14, said compound being 1-isopropylsulfonyl-2-amino-6-(α-methoxycarbonylmethylenebenzyl)benzimidazole.

16. The compound of claim 14, said compound being 1-isopropylsulfonyl-2-amino-6-(α-cyanomethylenebenzyl)benzimidazole.

17. The compound of claim 14, said compound being 1-isopropylsulfonyl-2-amino-6-[α-(cyclopropylmethoxycarbonylmethylene)benzyl]benzimidazole.

18. The compound of claim 14, said compound being 1-isopropylsulfonyl-2-amino-6-(α-bromomethylenebenzyl)benzimidazole.

19. The compound of claim 14, said compound being 1-isopropylsulfonyl-2-amino-6-(α-aminocarbonylmethylenebenzyl)benzimidazole.

20. The compound of claim 14, said compound being 1-isopropylsulfonyl-2-amino-6-(α-methylaminocarbonylmethylenebenzyl)benzimidazole.

21. The compound of claim 14, said compound being 1-isopropylsulfonyl-2-amino-6-(α-dimethylaminocarbonylmethylenebenzyl)benzimidazole.

22. The compound of claim 14, said compound being 1-isopropylsulfonyl-2-amino-6-[α-(2-dimethylaminoethoxycarbonyl)methylenebenzyl]benzimidazole.

23. The compound of claim 1 wherein $R^1$ is $C_1$–$C_4$ alkanoyl.

24. The compound of claim 23 wherein $R^7$ is phenyl.

25. The compound of claim 24, wherein $R^7$ is acetyl.

26. The compound of claim 1 wherein X is hydrogen and Y is hydroxy.

27. The compound of claim 26 wherein $R^7$ is phenyl.

28. The compound of claim 27 wherein $R^2$ is $-SO_2R^3$.

29. The compound of claim 27 wherein $R^2$ is $$\underset{(CH_2)_n}{\overset{N\diagup\diagdown S}{\diagdown\phantom{xx}\diagup}}\!\!-R^4.$$

30. The compound of claim 2 wherein $R^8$ and $R^9$ both are chloro or bromo.

31. A method of treating viral infections in mammals comprising administering to a subject suffering from a viral infection and in need of treatment or to a subject suspected of developing a viral infection an antiviral amount of a compound of claim 1.

32. The method according to claim 31 employing a compound wherein X and Y together are a bond.

33. The method according to claim 32 employing a compound wherein $R^1$ is hydrogen.

34. The method according to claim 33 employing a compound wherein $R^7$ is phenyl.

35. The method according to claim 34 employing a compound wherein $R^8$ and $R^9$ both are halo.

36. The method according to claim 34 employing a compound wherein one of $R^8$ and $R^9$ is hydrogen and the other is halo, cyano, or $COR^{10}$ wherein $R^{10}$ is $C_1$–$C_4$ alkoxy or $(O\text{–}C_1\text{–}C_4 \text{ alkyl})_y NR^{11}R^{12}$.

37. The method according to claim 34 employing a compound wherein $R^2$ is $-SO_2R^3$.

38. The method according to claim 34 employing a compound wherein $R^2$ is

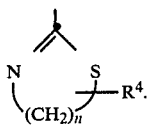

39. A pharmaceutical formulation useful in the treatment of viral infections comprising a benzimidazole of claim 1 in combination with a pharmaceutically acceptable diluent or carrier therefor.

40. The formulation according to claim 39 comprising a compound wherein X and Y together are a double bond.

41. The formulation according to claim 40 comprising a compound wherein $R^{11}$ is hydrogen.

42. The formulation according to claim 41 comprising a compound wherein $R^7$ is phenyl.

43. The formulation according to claim 42 comprising a compound wherein $R^8$ and $R^9$ both are halo.

44. The formulation according to claim 42 comprising a compound wherein one of $R^8$ and $R^9$ is hydrogen and the other is halo, cyano, or $COR^{10}$ wherein $R^{10}$ is $C_1$-$C_4$ alkoxy or $(O-C_1-C_4 \text{ alkyl})_y NR^{11}R^{12}$.

45. The formulation according to claim 42 comprising a compound wherein $R^2$ is $-SO_2R^3$.

46. The formulation according to claim 42 comprising a compound wherein $R^2$ is

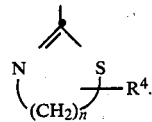

* * * * *